United States Patent

Junius et al.

Patent Number: 5,091,527
Date of Patent: Feb. 25, 1992

[54] SUBSTRATE FOR PHOSPHOLIPASE

[75] Inventors: Martina Junius, Bernried; Ulrich Neumann; Herbert von der Eltz, both of Weilheim, all of Fed. Rep. of Germany

[73] Assignee: Boehringer Mannheim GmbH, Mannheim, Fed. Rep. of Germany

[21] Appl. No.: 318,075

[22] Filed: Mar. 2, 1989

[30] Foreign Application Priority Data

Mar. 4, 1988 [DE] Fed. Rep. of Germany ....... 3807123

[51] Int. Cl.$^5$ ............... C07D 265/38; C07C 305/10; C07F 9/10
[52] U.S. Cl. .................... 544/102; 548/414; 548/484; 549/5; 549/7; 549/11; 549/33; 558/180; 558/169; 558/32
[58] Field of Search ............... 544/102; 548/414, 484; 549/5, 7, 11, 33; 558/180, 169, 32

[56] References Cited

U.S. PATENT DOCUMENTS 4,485,045 11/1984 Regen ................................. 260/403
4,847,376 7/1989 Neumann et al. ................. 544/102

FOREIGN PATENT DOCUMENTS 0070433 1/1983 European Pat. Off. .
0225129 6/1987 European Pat. Off. .
59-31786 2/1984 Japan ................................. 558/169

OTHER PUBLICATIONS

Kodama et al, Chem. Abstracts, vol. 108 (1988) p. 22209a.
Synthesis-Journal of Synthetic Organic Chemistry, Jan. (1987), No. 1, New York, NY, pp. 60-62.

Primary Examiner—Mary C. Lee
Assistant Examiner—Michael G. Ambrose
Attorney, Agent, or Firm—Felfe & Lynch

[57] ABSTRACT

The present invention provides phospholipase substrates of the general formula:

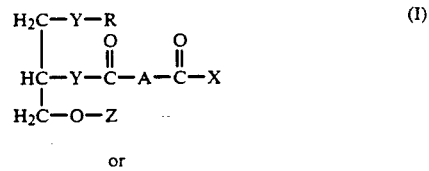

(I)

or

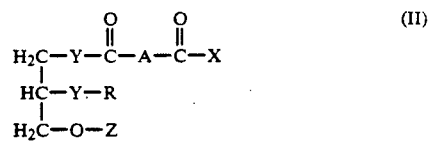

(II)

wherein A is an alkylene or alkenylene radical containing up to 16 carbon atoms, R is a hydrgen atom or an alkyl, alkenyl or acyl radical containing up to 20 carbon atoms or an optionally alkyl-substituted aryl or aralkyl radical containing up to 8 carbon atoms in the alkyl moiety, X is the residue of an aromatic hydroxy or thiol compound and each Y, independently of one another, is an oxygen or sulphur atom and Z is $-SO_3^\ominus$ or a radical of the general formula:

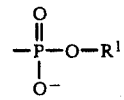

wherein $R^1$ can be a hydrogen atom or a radical of the general formula $-(CH_2)_n NR_3^2$, in which n is 2, 3 or 4 and $R^2$ is a hydrogen atom or a methyl radical, or is an inositol or serine ($-CH_2-CH(NH_2)-COOH$) or glycerol residue.

The present invention also provides a process for the optical determination of phospholipases using these substrates, as well as a reagent containing them.

8 Claims, No Drawings

SUBSTRATE FOR PHOSPHOLIPASE

The present invention is concerned with phospholipase substrates, a process for the optical determination of phospholipases and a reagent for carrying out the process.

Phospholipases (PL) catalyze the hydrolysis of ester groups of the sn-3-phosphoglycerides.

In aqueous solution, the substrates form micelles and the enzymes act on the lipid-water boundary surface.

The series of phospholipases are known which are of especial interest, in particular phospholipase C and phospholipase $A_2$, which are the best investigated PL of the human body. In the case of certain diseases, for example pancreatitis, infectious diseases, autoimmune diseases and allergies, the PL $A_2$ concentration in the blood and other body fluids increases. Therefore, the determination of the PL $A_2$ activity is of considerable diagnostic importance.

PL C and especially also phosphatidyl-inositol-specific PL C (PInase) has recently assumed increasing importance. The regulator system phosphatidyl-inositol is being intensively investigated by many research groups. Furthermore, PL C also plays a part in the dissolving off of membrane-bound proteins.

PL $A_2$ is also present in some snake venoms (cobra and rattlesnake) and an increased concentration thereof is a danger to life. PL $A_2$ belongs to the digestive enzymes and the determination thereof plays a great part not only in clinical chemistry but also in biochemistry, pharmaceutical chemistry and foodstuff chemistry (see G. E. Hoffmann, Dt. Ges. f. Klin. Chem. e.V.—Mitteilungen, 4, 196/1986).

Several phospholipase measurement methods are already known, for example the titrimetric determination of the fatty acids liberated by the ester cleavage (Figarella, Scand. J. Gastroent., 6, 133/1971) and the measurement of radioactively labelled liberated fatty acids (Shakir, Anal. Biochem., 114, 64/1981). However, these processes are very laborious and too prone to disturbance for routine purposes.

Further, photometric methods of determination are also known:
a) Hendrickson, J. Lipid Res., 24, 1532/1983;
b) Hoffmann, Dt. Ges. f. Klin. Chem., Mitteilungen, 4, 201/1986.

Method a) depends upon the liberation of an -SH group and the determination thereof with DTNB but proves to be too insensitive.

Method b) is a fully enzymatic method for the determination of fatty acids according to the firm Wako, Japan but is also laborious and very subject to disturbance (numerous pipetting steps). NEFA-C test.

Fluorescing phospholipids are also known as substrates (Thuren, Clin. Chem., 31, 714/1985). However, this method is also very subject to disturbances and not many laboratories are equipped with fluorescence measurement apparatus.

Immunological processes have also been described for the determination of PL A: Radioimmunoassay (Nishijima, J. Biochem., 94, 137/1983) and fluorescence immunoassay (Eskola, Clin. Chem., 29, 1777/1983) which admittedly suffice with regard to sensitivity but are not able to distinguish between the active phospholipase A and its inactive precursors.

Only a few methods are known for the determination of phospholipase C. Thus, it is known, after cleavage of the substrate by PL C, to liberate glycerol with lipase as auxiliary enzyme and then to carry out a fully enzymatic determination of the liberated glycerol (Wahlefeld in Bergmeyer: Methoden der enzymatischen Analyse, 3rd edition, Vol. II, pub. Verlag Chemie, Weinheim, 1974, p. 1878). However, this method is very subject to disturbance and is time-consuming.

The determination of PL C by the use of radioactively-labelled substrates has also been published (Waku, J. Biochem., 72, 149/1972). However, this method is laborious and insensitive.

Therefore, there is a need for a color test which can be carried out with the use of a simple apparatus and which can be directly monitored visually.

Therefore, it is an object of the present invention to provide a substrate and a color test for the determination of phospholipase with the use of a substrate which does not display the disadvantages of the known tests, provides precise results, is simple to use, has a high sensitivity and only possesses a small lag phase so that adaptation to various automatic analysis systems is not difficult.

Thus, according to the present invention, there are provided phospholipase substrates of the general formula:

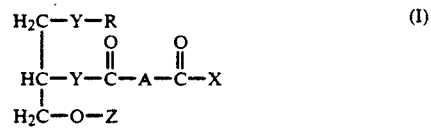

or

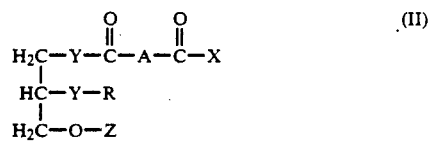

wherein A is an alkylene or alkenylene radical containing up to 16 carbon atoms, R is a hydrogen atom or an alkyl, alkenyl or acyl radical containing up to 20 carbon atoms or an optionally alkyl-substituted aryl or aralkyl radical containing up to 8 carbon atoms in the alkyl moiety, X is the residue of an aromatic hydroxy or thiol compound and each Y, independently of one another, is a sulphur or oxygen atom and Z is $-SO_3^\ominus$ or a radical of the general formula:

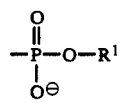

wherein $R^1$ can be a hydrogen atom or a $-(CH_2)_nNR_3^2$ radical, in which n is 2, 3 or 4 and $R^2$ is a hydrogen atom or a methyl radical, or is an inositol or serine ($-CH_2-CH(NH_2)-COOH$) or glycerol residue.

By means of the action of phospholipase, the substrate according to the present invention is cleaved with the liberation of the aromatic hydroxy or thiol compound corresponding to the radical R which is determined either directly optically or is coupled with an appropriate chromophore or fluorophore and the coupling product is measured or is possibly measured after the addition of an auxiliary enzyme.

R preferably contains 6 to 20 carbon atoms and especially preferably 12 to 18 carbon atoms. Surprisingly, we have found that the compounds in which R is an alkyl, alkenyl or aralkyl radical are good phospholipase substrates although the natural substrates carry acyl radicals.

Examples of R include methyl, ethyl, propyl, butyl, pentyl, hexyl, heptyl, octyl, nonyl, decyl, undecyl, dodecyl, tetradecyl, hexadecyl and octadecyl radicals as alkyl radicals, as well as the corresponding acyl radicals, for example acetyl, propionyl, butyryl, valeryl, capronyl, capryl, caprinyl, lauryl, myristyl, palmityl and stearyl radicals, as well as oleyl, crotonyl, linolyl radicals and also phenyl, benzyl and octylphenyl radicals.

The phospholipase substrates according to the present invention also contain the residue of a dicarboxylic acid of the general formula HOOC—A—COOH, in which A preferably contains 3 to 7 carbon atoms. Examples of acids from which A is derived include malonic acid, succinic acid, glutaric acid, adipic acid, pimelic acid, suberic acid, azelaic acid, sebacic acid, nonane dicarboxylic acid, decanedicarboxylic acid and undecanedicarboxylic acid, the acids from glutaric acid to azelaic acid being preferred. When A contains more than 4 carbon atoms, the addition of an auxiliary enzyme is recommendable.

X can be an aromatic hydroxy or thiol compound which represents a chromophore or can first be converted into a coloured material by a subsequent reaction. Typical examples thereof include phenol, thiophenol, naphthol, thionaphthol and derivatives thereof, as well as per se chromogenic compounds, such as resorufin, chlorophenol red, indoxyl or thiofluorescein radicals. Because of the large number thereof, an exhaustive listing of appropriate hydroxy and thiol compounds is not possible but the aromatic hydroxy and thiol compounds which are directly chromophoric or can be converted into chromophores are well known in the art.

The mentioned subsequent reaction to give a colored material can take place either by a direct coupling, for example with a diazonium salt, such as 4-chloro-2-methylbenzene diazonium salt (Fast Red), 4-benzamido-2-methoxy-5-methylbenzene diazonium salt (Fast Violet), diazotised sulphanilic acid or 2,4- or 2,5-substituted phenyldiazonium salts, such as 2,4-dichlorophenyldiazonium-1,5-naphthalene-disulphonic acid, or can take place by an oxidative coupling, for example with 4-aminoantipyrine or another aminopyrazolone, such as trimethylaminopyrazolone or diaminoantipyrine, or with 3-methyl-2-benzothiazolinonehydrazone-6-sulphonic acid (MBTHS).

Chromophores are preferred which have a low polarity and are lipophilic. However, the water solubility should thereby still be ensured.

The lipophilic character of the above-mentioned chromophores can be positively influenced by appropriate substitution, for example with alkyl radicals. Inter alia, methyl, dimethyl and ethyl radicals have proved to be appropriate substituents for the resorufin radicals, as well as substitution with bromine.

The compounds according to the present invention are new. They possess a centre of asymmetry and are, therefore, optically active. As phospholipase substrates, there can be used not only the racemates usually obtained in the case of the methods of preparation but also the optical isomers, which are preferred.

The preparation of the phospholipase substrates according to the present invention can take place in known manner. Thus, for example, appropriate processes for the synthesis of the ether-glycero- and acyl-glycerophosphocholines are described in Methods in Enzymology, 98, 623/1983 and in Biochim. Biophys. Acta, 666, 230/1981. The synthesis of the sulphates is described, for example, in Beilstein, 2, EII, 356.

Starting from described 1-alkyl or 1-acyl-3-O-tritylglycerol compounds, there are then obtained the corresponding glycerodicarboxylic acid monoesters by reaction with an appropriate dicarboxylic acid anhydride in an anhydrous medium, such as chloroform/pyridine. Appropriate methods for the preparation of the dicarboxylic acid anhydrides are described in HoubenWeyl-Müller, "Methoden der organischen Chemie", Vol. IV/4, p. 786.

Instead of the 3-0-trityl radical, other protective groups can also be used, for example the benzyl radical.

The esterification of the monoester with the aromatic hydroxy or thiol compound from which the radical X is derived can be carried out, for example, by direct reaction of the dicarboxylic acid monoester with the aromatic alcohol or thiol in the presence of an agent removing water, for example dicyclohexylcarbodiimide. Alternatively, the dicarboxylic acid monoester is first converted into an activated ester, for example into a hydroxysuccinimide ester or the imidazolide, and the activated ester is then reacted with the aromatic alcohol or thiol.

It is also possible first to prepare a monoester of the dicarboxylic acid with the aromatic alcohol or thiol, for example adipic acid mononitrophenyl ester or glutaric acid monophenyl ester, and then to esterify this with the alkyl or acyl glycerol, for example with the intermediate formation of an acid chloride, anhydride or activated ester. The preparation of the dicarboxylic acid monoester with the aromatic alcohol or thio can take place, for example, from the acid anhydride and aromatic compound in a mole ratio of 1:1 or from the dicarboxylic acid and aromatic compound in a mole ratio of 2:1 or from a dicarboxylic acid monoester with readily removable protective group and the aromatic compound. An appropriate method is described, for example, in Arch. Pharm., 287, 514/1954.

Alternatively, the 1-O-alkyl- or 1-O-acyl-3-O-tritylglycerodicarboxylic acid monoester can also be prepared by first preparing a dicarboxylic acid monoester from the dicarboxylic acid and an easily removable alcohol, for example benzyl alcohol or 2,2,2-trichloroethanol, and the so obtained acid is then esterified with the mentioned alkyl- or acyl-3-O-trityl-glycerol. Subsequently, the protective group is removed and the reaction with the aromatic alcohol or thiol carried out as described above.

In the case of the above-described products, the protective groups are then to be split off and the C-3-OH position sulphated or phosphorylated.

A further method of preparation consists in first reacting a protected glycerol, such as 1,2-isopropylideneglycerol, with a dicarboxylic acid monoester with the formation of the correspondingly protected glycero-3-dicarboxylic acid diester, then removing the protective group of the glycerol and alkylating or acylating the liberated 1—OH and 2—OH groups. Finally, the first introduced monoester group (carboxyl protective group) is split off, followed by reaction with the aromatic alcohol or thiol. After splitting off the protective group on C—1—OH, it is phosphated or sulphated.

Furthermore, the desired substrate can be prepared starting from appropriate lyso compounds, such as 1-alkyl-glycero-3-sulphates, for example by reaction with an activated dicarboxylic acid monoester.

The above-described preparation of the substrates according to the present invention is not exhaustive and numerous other known methods are available for the ready preparation of the compounds according to the present invention. From the racemic products obtained according to the above-described processes there can, if desired, be obtained the pure optical isomers according to known separation processes. In the same way, the isomers can, however, also be obtained by stereospecific syntheses according to processes which are also known.

According to the present invention, there is also provided a process for the optical determination of phospholipases, wherein a phospholipase substrate according to the present invention is subjected to the action of a phospholipase-containing sample and the amount of liberated aromatic hydroxy or thiol compound optically determined directly or the colour formed therefrom after coupling with an appropriate chromogen. The addition of one or two auxiliary enzymes is possibly necessary.

This determination process is preferably carried out with a calcium concentration in the test of from 0.5 to 10 mM/liter.

Furthermore, the present invention provides a simple and readily stable reagent for the optical determination of phospholipase which, besides a phospholipase substrate according to the present invention and a buffer substance, also contains a surface-active agent, especially a bile acid salt, a chromogenic coupler and/or a salt, such as calcium chloride. Furthermore, the reagent advantageously also contains a preserving agent and/or an activator.

A preferred composition of this reagent contains:
0.05–10 mg./ml. of substrate and preferably 0.5–10 mg./ml. of substrate,
2–50 mg./ml. bile acid,
0.5–10 mM/l. calcium ions (activator), preferably calcium chloride,
0–10 g./l. detergent,
20–250 mM/l. buffer substance,
in each case referred to the solution ready for use in the test.

As surface-active agent of the bile acid group, there can be used, for example, cholic acid, taurocholic acid, desoxycholic acid, taurodesoxycholic acid or glycodesoxycholic acid or an alkali metal salt thereof and especially a sodium salt thereof. The preferred amount of the surface-active agent is from 0.5 to 1.5 mM/liter. Alternatively or additionally, the reagent can also contain one or more non-ionic detergents.

As detergents, there can be used not only ionic but also non-ionic detergents. Preferably there are used non-ionic detergents, for example Triton ® (alkylaryl polyethers). The concentration range is preferably from 0 to 10 g./liter and especially preferably from 1 to 5 g./liter.

Appropriate buffer substances are those which are able to adjust a pH value of from 6.0 to 10.5 in the reagent according to the present invention, the preferred pH value range being from 7.0 to 9.5. Examples of appropriate buffers include diethanolamine buffer, triethanolamine buffer, Tris buffer and Good buffers, such as Hepes buffer (very appropriate for addition before lyophilisation), Taps buffer, CHES buffer (2-(cyclohexylamino)-ethanesulphonic acid) and bicine, Tris buffer being especially preferred. The preferred amount of buffer is from 20 to 250 mM/liter.

As preserving agents in the scope of the present invention, those are used which do not impair the enzymatic activity of the phospholipase to be determined. Alkali metal azides are especially appropriate, particularly sodium azide. Other preserving agents, for example thiozide and other sulphur-containing preserving agents, can, however, also be used. The preferred amount of preserving agent is from 0.001 to 2 mg./ml.

As activators, there can be used alkaline earth metal ions and preferably calcium ions. Since these form insoluble compounds with desoxycholic acid, in the case of the presence of calcium, it is preferred to use taurodesoxycholic acid as bile acid since this permits the use of higher calcium concentrations in the range of from 1 to 5 mMole.

If the reagent according to the present invention is used in dry or concentrated form intended for dilution to the composition to be finally employed, then it contains the mentioned substances in appropriate amount ratios, as well as preferably protective colloids.

As protective colloids, there can be used the substances known for this purpose, such as polyhydroxy compounds, serum albumin, polyvinylpyrrolidone, solid polyethylene oxides and the like. Polyhydroxy compounds are preferred and especially monomeric or polymeric pentoses or hexoses with 1 to 10 pentose or hexose units in the molecule and/or polyethylene glycols which are solid at ambient temperature. Preferred examples of appropriate polyhydroxy compounds include mannitol and similar sugar alcohols, oligosaccharides of glucose, mannose, maltohaptaose, polyethylene glycol with an average molecular weight of from 3500 to 7000 and the like. Other protective colloids which can be used include, for example, amino acids, such as alanine, and vegetable gums, such as gum arabic and the like. The preferred amount of protective colloid or of a mixture of protective colloids is from 20 to 90% by weight. A mixture of a sugar alcohol and a polyalkylene glycol has proved to be especially useful.

The reagent according to the present invention can be present impregnated on an appropriate carrier material. There can be used not only absorbent carrier materials but also swellable, soluble film-forming carrier materials. In this form, the reagent according to the present invention makes possible the production of test strips which can be evaluated directly visually or by means of appropriate measurement apparatus.

The colour test according to the present invention for the determination of phospholipases provides very exact results in the case of high sensitivity. It is very simple to use and is even appropriate for test strips. Since it only displays a very small lag phase or even no lag phase at all, it can readily be adapted to various automatic analysis systems.

The determination itself can be carried out not only as an end point determination but also kinetically. In comparison with many of the known processes, an advantage of being able to carry out the test kinetically is that neither a stopping nor an extraction of the reaction product has to be carried out.

The following Examples are given for the purpose of illustrating the present invention:

EXAMPLE 1

1-0-Octadecyl-2-glutaric acid p-nitrophenyl ester sn-glycero-3-phosphocholine a) 1-0-Octadecyl-2-glutaric acid sn-glycero-3-phosphocholine 1 g. 1-0-Octadecyl-sn-glycero-3-phosphocholine, 0.73 g. glutaric acid anhydride and 0.2 g. dimethylaminopyridine are heated to 50° C. for 70 hours in 30 ml. pyridine. The solvent is then stripped off and the residue chromatographed over LH 20 (elution agent: chloroform/methanol 1:1 v/v). It is subsequently chromatographed over RP 18 (elution agent: isopropanol/water 9:1 v/v). Yield: 0.87 g.

TLC: $R_f=0.26$ (silica gel; methanol) spray reagent: Hanes-Isherwood reagent.

$^1$H-NMR (CDCl$_3$): δ ppm: 0.87 (t, 3H); 1.26 (m, 32H); 1.90 (m, 2H); 2.4 (m, 4H); 3.1-3.6 (m, 13H); 3.78 (m, 2H); 4.02 (m, 2H); 4.25 (m, 2H); 5.18 (m, 1H).

b) 1-0-Octadecyl-2-glutaric acid p-nitrophenyl ester sn-glycero-3-phosphocholine 310 mg. of the product from Example 1a) are dissolved in a mixture of water/tetrahydrofuran (1:1 v/v) and mixed with 70 mg. p-nitrophenol and 480 mg. N-ethyl-N'-dimethylaminopropyl carbodiimide. The reaction mixture is subsequently stirred for 40 hours at 60° C. After evaporation of the solvent, the residue is chromatographed over RP 18 (elution agent: isopropanol/water 8:2 v/v).

TLC: $R_f=0.21$ (RP 18; isopropanol/water 8:2 v/v).

$^1$H-NMR (CDCl$_3$): δ ppm: 0.88 (t, 3H); 1.25 (m, 32H); 2.04 (m, 2H); 2.2-2.8 (m, 4H); 3.1-3.6 (m, 13H); 3.80 (m, 2H); 3.96 (m, 2H); 4.28 (m, 1H); 5.15 (m, 1H); 7.30 (d, 2H); 8.26 (d, 2H).

EXAMPLE 2

1-0-Octadecyl-2-glutaric acid methylresorufin ester sn-glycero-3-phosphocholine

The preparation is analogous to Example 1b) from 31 mg. of the product of Example 1a), 10 ml. water/tetrahydrofuran (1:1 v/v), 110 mg. 4-methylresorufin and 48 mg. N-ethyl-N'-dimethylaminopropyl carbodiimide.

TLC: $R_f=0.20$ (RP 18; isopropanol/water 8:2 v/v).

$^1$H-NMR (d$_4$-methanol): δ ppm: 0.90 (t, 3H); 1.28 (m, 32H); 1.92 (m, 2H); 2.16 (s, 3H); 2.44 (m, 4H); 3.51 (m, 2H); 3.69 (m, 11H); 4.00 (m, 2H); 4.29 (m, 2H); 4.47 (m, 2H); 5.2 (m, 1H); 6.7-7.9 (m, 5H).

EXAMPLE 3

1-0-Dodecyl-2-glutaric acid p-nitrophenyl ester glycero-3-sulphate a) 1-0-Dodecyl-2-glutaric acid 3-0-tritylglycerol 20.1 g. 1-0-Dodecyl-3-0-tritylglycerol, 9.2 g. glutaric acid anhydride and 0.4 g. dimethylaminopyridine are heated to 50° C. for 8 hours in 100 ml. pyridine. The solvent is stripped off and the residue is taken up in ethyl acetate and shaken up with 0.05N hydrochloric acid. After drying the ethyl acetate phase over anhydrous sodium sulphate, the solvent is evaporated off the residue chromatographed on silica gel (elution agent: ethyl acetate/petroleum ether 1:4 v/v). Yield: 14 g.

TLC: $R_f=0.20$ (silica gel; ethyl acetate/petroleum ether 1:1 v/v).

$^1$H-NMR (CDCl$_3$): δ ppm: 0.88 (t, 3H); 1.25 (m, 20H); 1.99 (q, 2H); 2.43 (t, 4H); 3.15-3.45 (m, 4H); 3.59 (d, 2H); 5.22 (m, 1H); 7.3 (m, 15H).

b) 1-0-Dodecyl-2-glutaric acid p-nitrophenyl ester 3-0-tritylglycerol 8.6 g. of the product from Example 3a) are dissolved in 150 ml. chloroform and 1.94 g. p-nitrophenol and 14.4 g. dicyclohexylcarbodiimide successively added thereto. After stirring the reaction mixture for 12 hours at ambient temperature, the precipitate is filtered off and the filtrate evaporated. The residue is chromatographed on silica gel (elution agent: ethyl acetate/petroleum ether 1:4 v/v). Yield: 8.8 g.

TLC: $R_f=0.42$ (silica gel; ethyl acetate/petroleum ether 1:4 v/v).

$^1$H-NMR (CDCl$_3$): δ ppm: 0.88 (t, 3H); 1.25 (m, 20H); 2.12 (q, 2H); 2.53 (t, 2H); 2.71 (t, 2H); 3.2-3.5 (m, 4H); 3.59 (d, 2H); 5.28 (m, 1H); 7.18 (d, 2H); 7.30 (m, 15H); 8.20 (d, 2H).

c) 1-0-Dodecyl-2-glutaric acid p-nitrophenyl ester glycerol 6 g. of the product from Example 3c) are dissolved in petroleum ether and applied to silica gel which has been treated with boric acid. The product is washed down with petroleum ether/ethyl acetate (8:2 v/v).

Yield: 2.7 g.

TLC: $R_f=0.21$ (silica gel; chloroform/acetone 49:1 v/v).

$^1$H-NMR (CDCl$_3$): δ ppm: 0.87 (t, 3H); 1.25 (m, 20H); 2.10 (m, 2H); 2.53 (t, 2H); 2.71 (t, 2H); 3.45 (t, 2H); 3.63 (d, 2H); 3.82 (d, 2H); 5.04 (m, 1H); 7.28 (d, 2H); 8.26 (d, 2H).

d) 1-0-Dodecyl-2-glutaric acid p-nitrophenyl ester glycero-3-sulphate 500 mg. of the product from Example 3c) are taken up in 4 ml. chloroform and mixed with 0.22 ml. pyridine. 0.18 ml. Chlorosulphonic acid in 2 ml. chloroform are added dropwise thereto, with ice cooling. The reaction solution is then further stirred for 2 hours at 0° C. and for 1 hour at ambient temperature. After the addition of 2 drops of water, it is evaporated and the residue taken up in chloroform. After drying over anhydrous sodium sulphate, the solvent is evaporated off and the residue chromatographed on silica gel (elution agent: methylene chloride/methanol 8:1 v/v).

Yield: 180 mg.

TLC: $R_f=0.26$ (silica gel; methylene chloride/methanol 6:1 v/v).

$^1$H-NMR (CDCl$_3$): δ ppm: 0.89 (t, 3H); 1.21 (m, 20H); 2.02 (m, 2H); 2.54 (m, 4H); 3.45 (m, 4H); 4.19 (m, 2H); 5.33 (m, 1H); 7.28 (d, 2H); 8.22 (d, 2H).

EXAMPLE 4

1-0-Hexadecyl-2-glutaric acid p-nitrophenyl ester glycero-3-sulphate a) 1-0-Hexadecyl-2-glutaric acid 3-0-tritylglycerol This is prepared analogously to Example 3a) from 15 g. 1-0-hexadecyl-3-0-tritylglycerol, 50 ml. pyridine, 6.2 g. glutaric acid anhydride and 0.4 g. dimethylaminopyridine. Yield: 7.14 g.

TLC: $R_f=0.35$ (silica gel; ethyl acetate/petroleum ether 2:3 v/v).

$^1$H-NMR (CDCl$_3$): δ ppm: 0.87 (t, 3H); 1.1-1.65 (m, 28H); 2.0 (m, 2H); 2.43 (t, 4H); 3.32 (m, 4H); 3.59 (d, 2H); 5.21 (m, 1H); 7.33 (m, 15H).

b) 1-0-Hexadecyl-2-glutaric acid p-nitrophenyl ester 3-0-tritylglycerol

This is prepared analogously to Example 3b) from 3.5 g. of the product of Example 4a), 50 ml. chloroform, 0.84 g. p-nitrophenol and 6.18 g. dicyclohexylcarbodiimide. Yield: 2.85 g.

TLC: $R_f=0.47$ (silica gel; ethyl acetate/petroleum ether 1:4 v/v).

$^1$H-NMR (CDCl$_3$): δ ppm: 0.88 (t, 3H); 1.25 (m, 28H); 2.13 (q, 2H); 2.53 (t, 2H); 2.7 (t, 2H); 3.33 (m, 4H); 3.59 (d, 2H); 5.28 (m, 1H); 7.17 (d, 2H); 7.33 (m, 15H); 8.20 (d, 2H).

c) 1-O-Hexadecyl-2-glutaric acid p-nitrophenyl ester glycerol

This is prepared analogously to Example 3c). from 2.8 g. of the product of Example 4b). Yield: 1.8 g.

TLC: $R_f=0.22$ (silica gel; chloroform/acetone 49:1 v/v).

$^1$H-NMR (CDCl$_3$): δ ppm: 0.87 (t, 3H); 1.25 (m, 28H); 2.12 (q, 1H); 2.55 (m, 4H); 3.35–4.0 (m, 6H); 5.1 (m, 1H); 7.28 (d, 2H); 8.27 (d, 2H).

d) 1-O-Hexadecyl-2-glutaric acid p-nitrophenyl ester glycero-3-sulphate

This is prepared analogously to Example 3d) from 500 mg. of the product from Example 4c). Yield: 310 mg.

TLC: $R_f=0.30$ (silica gel; methylene chloride/methanol 8:1 v/v).

$^1$H-NMR (CDCl$_3$): δ ppm: 0.87 (t, 3H); 1.24 (m, 28H); 2.03 (m, 2H); 2.3–2.8 (m, 4H); 3.20–3.70 (m, 4H); 4.19 (m, 2H); 5.31 (m, 1H); 7.29 (d, 2H); 8.23 (d, 2H).

EXAMPLE 5

1-O-Dodecyl-2-adipic acid p-nitrophenyl ester glycero-3-sulphate a) 1-O-Dodecyl-2-O-benzylglycero-3-sulphate 28 g. 1-O-Dodecyl-2-O-benzylglycerol are dissolved in 200 ml. chloroform, 20 ml. pyridine are added thereto and a solution of 11.2 ml. chlorosulphonic acid in 80 ml. chloroform added dropwise thereto at 0° C. Subsequently, the reaction mixture is stirred for 3 hours at ambient temperature and the mixture then poured on to ice. The aqueous phase is shaken out three times with chloroform and the organic phase, after drying over anhydrous sodium sulphate, is evaporated. The residue is chromatographed on silica gel (elution agent: chloroform/methanol 4:1 v/v). Yield: 23 g.

TLC: $R_f=0.25$ (silica gel; methylene chloride/methanol 9:1 v/v) (spray reagent: dichlorofluorescein).

$^1$H-NMR (CDCl$_3$): δ ppm: 0.88 (t, 3H); 1.24 (m, 20H); 3.15–3.50 (m, 4H); 3.74 (m, 1H); 4.0 (s, 1H); 4.22 (m, 2H); 4.59 (s, 1H); 4.64 (s, 1H); 7.26 (m, 5H).

b) 1-O-Dodecylglycero-3-sulphate 22.8 g. of the product from Example 5a) are dissolved in 500 ml. methanol and hydrogenated in the presence of 2.3 g. palladium/charcoal, the course of the reaction being monitored by TLC. After completion of the reaction, the reaction mixture is filtered and the filtrate evaporated. The residue is slurried in acetone and filtered off. Yield: 15.6 g.

TLC: $R_f=0.34$ (silica gel; methylene chloride/methanol 4:1 v/v).

$^1$H-NMR (d$_4$-methanol): δppm: 0.89 (t, 3H); 1.28 (m, 20H); 3.4–3.6 (m, 4H); 3.9–4.1 (m, 3H).

c) p-Nitrophenyl-adipic acid anhydride 1 g. p-Nitrophenyl adipate is stirred for 2 hours at 80° C. in 40 ml. acetic anhydride. Subsequently, the solvent is stripped off and the residue dried in a high vacuum. The crude product obtained is further reacted. TLC: $R_f=0.6$ (silica gel; ethyl acetate).

d) 1-O-Dodecyl-2-adipic acid p-nitrophenyl ester glycero-3-sulphate 0.44 g. each of the products of Examples 5b) and 5c) and 100 g. dimethylaminopyridine are stirred for 5 hours at 80° C. in 50 ml. pyridine. After stripping off the solvent, the residue is chromatographed on silica gel (elution agent: chloroform/methanol 6:1 v/v).

Yield: 100 mg.

TLC: $R_f=0.29$ (silica gel; chloroform/methanol 6:1 v/v).

$^1$H-NMR (CDCl$_3$): δ ppm: 0.86 (t, 3H), 1.23 (m, 20H); 1.73 (m, 4H); 2.20–2.75 (m, 4H); 3.2–3.7 (m, 4H); 4.16 (m, 2H); 5.31 (m, 11H); 7.29 (d, 2H); 8.24 (d, 2H).

EXAMPLE 6

Solution 1:

125 mM Tris buffer (pH 7.1), 4.0 mM calcium chloride, 250 μl./100 ml. Triton X-100 and 41 mg./100 ml. sodium desoxycholate.

Solution 2:

1 ml. of Solution 1 is stirred with 2 mg. of substrate 1-O-hexadecyl-2-glutaric acid nitrophenyl ester rac-glycero-3-sulphate with gentle heating until an emulsion is formed.

20 μl. of sample (enzyme solution) are added hereto. The course of the reaction is monitored photometrically at λ=405 nm.

In the case of the evaluation via a standard of known phospholipase activity, the phospholipase activity of the sample is calculated as follows:

$$\text{activity}_{(sample)} = \frac{\text{activity}_{(standard)} \times \Delta E/\text{min. (sample)}}{\Delta E/\text{min. (standard)}}$$

A calculation of the phospholipase activity of the sample is also possible according to the following equation:

$$\text{activity}_{(sample)}[U/l.] = 1000 \times \frac{V_{total}}{\epsilon \times V_{sample} \times d} \times \Delta E/\text{min.}$$

$V_{total}$=total volume of the test batch [cm$^3$]
$V_{sample}$=volume of the sample [cm$^3$]
$\epsilon$=extinction coefficient of the chromogen at 405 nm
$d$=layer thickness of the cuvette [cm]
$\Delta E/\text{min.}$=extinction change per minute at 405 nm.

In the case of the mentioned reaction conditions, the extinction coefficient $\epsilon=9.0$. cm$^2$. μMole$^{-1}$.

It will be understood that the specification and examples serve to illustrate the invention and are not to be understood to limit the invention. Other embodiments within the spirit and scope of the invention will suggest themselves to those skilled in the art.

We claim:

1. A phospholipase substrate of the formula:

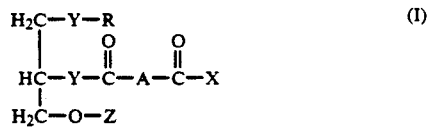

or

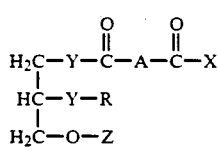

(II)

wherein

A is a $C_1-C_{16}$ alkylene or alkenylene,

R is hydrogen or A $C_1-C_{20}$ alkyl, alkenyl or acyl or R is unsubstituted or alkyl-substituted aryl or aralkyl containing up to 8 carbon atoms in the alkyl moiety, X is the residue of an aromatic hydroxy or thiol compound selected from the group consisting of resorufin, chlorophenol red, indoxyl, naphthol, thiophenol, thiofluorescein, and phenol, wherein X is optionally substituted with an alkyl group, a nitro group, or a bromine atom, and each Y, independently of one another, is an oxygen or sulphur atom, and Z is $-SO_3^-$ or a group of the formula:

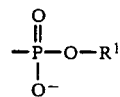

wherein $R^1$ is hydrogen or a group of the formula $-(CH_2)_n R_3^2$, $nNR_3^2$ in which n is 2, 3 or 4 and $R^2$ is hydrogen, methyl or $R^2$ is an inositol, serine ($-CH_2-CH(NH_2)-COOH$) or glycerol residue.

2. The phospholipase substrate of claim 1, wherein R contains 8 to 20 carbon atoms.

3. The phospholipase substrate of claim 1 or 2, wherein A contains 3 to 7 carbon atoms.

4. A phospholipase substrate designated 1-0-Octadecyl-2-glutaric acid methylresorufin ester sn-glycero-3-phosphocholine.

5. A phospholipase substrate designated 1-0-Octadecyl-2-glutaric acid p-nitrophenyl ester sn-glycero-3-phosphocholine.

6. A phospholipase substrate designated 1-0-Dodecyl-2-glutaric acid nitrophenyl ester rac-glycero-3-sulphate.

7. A phospholipase substrate designated 1-0-Dodecyl-2-adipic acid nitrophenyl ester rac-glycero-3-sulphate.

8. A phospholipase substrate designated 1-0-Hexadecyl-2-glutaric acid nitrophenyl ester rac-glycero-3-sulphate.

* * * * *

UNITED STATES PATENT AND TRADEMARK OFFICE
CERTIFICATE OF CORRECTION

PATENT NO.   :   5,091,527

DATED        :   February 25, 1992

INVENTOR(S)  :   Martina Junius, et al.

It is certified that error appears in the above-identified patent and that said Letters Patent is hereby corrected as shown below:

Col. 12, line 9:
   Claim 1        change "$(CH_2)_n R_3^2, nNR_3^2$"        to
                  -- $(CH_2)_n NR_3^2$ --.

Signed and Sealed this

Nineteenth Day of October, 1993

Attest:

BRUCE LEHMAN

Attesting Officer    Commissioner of Patents and Trademarks